United States Patent
Ko

(10) Patent No.: US 8,439,956 B2
(45) Date of Patent: May 14, 2013

(54) METHOD OF PERFORMING A DECOMPRESSIVE CRANIECTOMY

(75) Inventor: Kathryn Ko, New York, NY (US)

(73) Assignee: Gyrus Productions, Inc., Bellport, NY (US)

( * ) Notice: Subject to any disclaimer, the term of this patent is extended or adjusted under 35 U.S.C. 154(b) by 1108 days.

(21) Appl. No.: 11/749,990

(22) Filed: May 17, 2007

(65) Prior Publication Data

US 2007/0293865 A1   Dec. 20, 2007

Related U.S. Application Data

(60) Provisional application No. 60/812,105, filed on Jun. 9, 2006.

(51) Int. Cl.
*A61B 17/88* (2006.01)
*A61B 17/80* (2006.01)

(52) U.S. Cl.
USPC ............................ 606/281; 606/286; 606/903

(58) Field of Classification Search ............. 16/221, 16/234, 374, 382, 384–385, 387, 389; 128/898; 600/104–105; 604/22; 606/45–46, 70–71, 606/82–84, 280–281, 286, 298, 301, 312, 606/902–903; 623/17.19
See application file for complete search history.

(56) References Cited

U.S. PATENT DOCUMENTS

| | | | |
|---|---|---|---|
| 2,440,123 A | 4/1948 | Smith | |
| 2,500,993 A | 3/1950 | Mason | |
| 3,488,779 A | 1/1970 | Christensen | |
| 4,096,857 A | 6/1978 | Cramer et al. | |
| 4,696,293 A | 9/1987 | Ciullo | |
| 5,443,516 A | 8/1995 | Albrektsson et al. | |
| 5,554,194 A | 9/1996 | Sanders | |
| 5,556,687 A * | 9/1996 | McMillin | 428/113 |
| 5,558,674 A * | 9/1996 | Heggeness et al. | 606/278 |
| 5,628,748 A * | 5/1997 | Vicari | 606/79 |
| 5,916,217 A * | 6/1999 | Manthrop et al. | 606/75 |
| 5,961,519 A * | 10/1999 | Bruce et al. | 606/280 |
| 5,993,448 A | 11/1999 | Remmier | |
| 6,053,915 A | 4/2000 | Bruchmann | |
| 6,187,004 B1 | 2/2001 | Fearon | |
| 6,340,362 B1 | 1/2002 | Pierer et al. | |
| 6,355,036 B1 * | 3/2002 | Nakajima | 606/57 |
| 6,537,275 B2 | 3/2003 | Venturini et al. | |
| 6,656,179 B1 | 12/2003 | Schaefer et al. | |
| 6,679,885 B2 * | 1/2004 | Wellisz | 606/75 |
| 6,764,489 B2 | 7/2004 | Ferree | |
| 6,852,113 B2 | 2/2005 | Nathanson et al. | |
| 6,872,210 B2 * | 3/2005 | Hearn | 606/71 |

(Continued)

OTHER PUBLICATIONS

International Preliminary Report on Patentability issued in Application No. PCT/US07/069142 mailed Dec. 24, 2008.

(Continued)

*Primary Examiner* — Nicholas Woodall
*Assistant Examiner* — Larry E Waggle, Jr.
(74) *Attorney, Agent, or Firm* — DLA Piper LLP (US)

(57) ABSTRACT

A method of performing a decompressive craniectomy includes removing a bone flap from a cranium, attaching one end of a movable plate to one end of the bone flap, and attaching another end of the movable plate to the cranium. The movable plate is configured to allow the bone flap to move to accommodate swelling of intracranial contents.

37 Claims, 3 Drawing Sheets

U.S. PATENT DOCUMENTS

| | | |
|---|---|---|
| 6,923,812 B1 | 8/2005 | Wellisz |
| 2002/0099395 A1* | 7/2002 | Acampora et al. ............ 606/157 |
| 2003/0100900 A1* | 5/2003 | Wellisz ............................ 606/72 |
| 2003/0225407 A1 | 12/2003 | Estrada |
| 2003/0229348 A1 | 12/2003 | Sevrain |
| 2003/0233093 A1 | 12/2003 | Moles et al. |
| 2004/0044345 A1* | 3/2004 | DeMoss et al. ................. 606/73 |
| 2004/0102776 A1 | 5/2004 | Huebner |
| 2004/0102778 A1 | 5/2004 | Huebner et al. |
| 2004/0176764 A1 | 9/2004 | Dant |
| 2005/0165484 A1 | 7/2005 | Ferree |
| 2005/0256526 A1 | 11/2005 | Johnston |
| 2008/0200954 A1* | 8/2008 | Tucci ............................. 606/280 |

OTHER PUBLICATIONS

International Search Report issued in Application No. PCT/US07/069142 dated Apr. 17, 2008.

Written Opinion issued in Application No. PCT/US07/069142 dated. Apr. 17, 2008.

Schmidt, John H. et al., Use of hinge craniotomy for cerebral decompression, Journal of Neurosurgery, Sep. 2007, vol. 107, No. 3, pp. 678-681.

Decreasing the Morbidity of Decompressive Craniectomy: The Tucci Flap, The Journal of Trauma, 2007, vol. 62, pp. 77-778.

\* cited by examiner

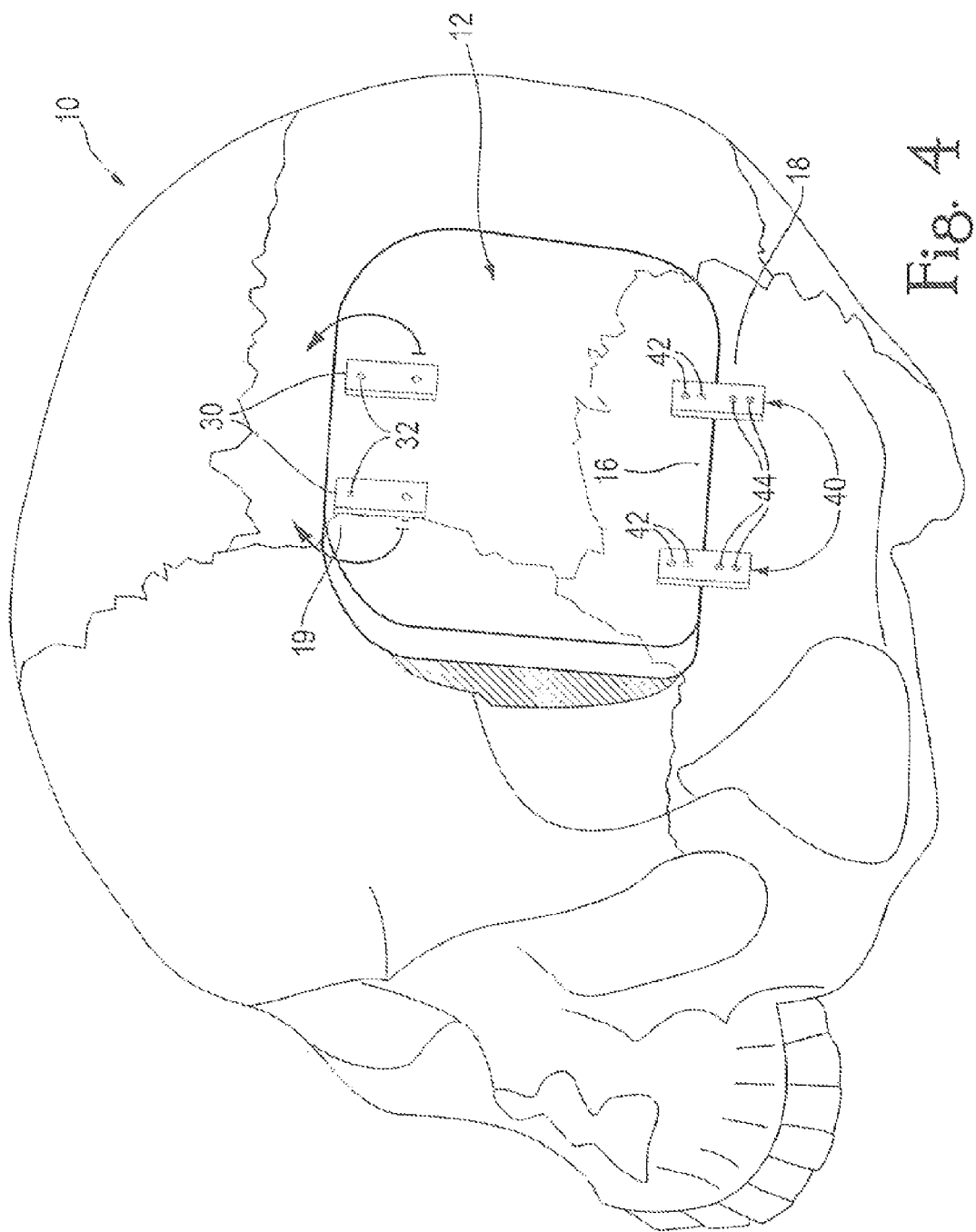

METHOD OF PERFORMING A DECOMPRESSIVE CRANIECTOMY

RELATED APPLICATIONS

The present application claims the benefit of U.S. Provisional Application No. 60/812,105, filed Jun. 9, 2006, which is incorporated by reference herein in its entirety.

FIELD OF THE INVENTION

The present invention relates generally to cranial surgery and more particularly to a method of performing a decompressive craniectomy.

BRIEF SUMMARY

An aspect of the present invention is to provide a method of performing a decompressive craniectomy. The method includes removing a bone flap from a cranium, attaching one end of a movable plate to one end of the bone flap, and attaching another end of the movable plate to the cranium. The movable plate is configured to allow the bone flap to move to accommodate swelling of intracranial contents.

BRIEF DESCRIPTION OF THE DRAWINGS

FIG. 4 depicts a bone flap attached to a cranium using a movable rigid plate, according to an alternative embodiment of the present invention.

DESCRIPTION OF EMBODIMENTS OF THE INVENTION

When the cranium (skull) and/or brain suffer injury in circumstances such as, for example, in accidents (e.g., motor vehicle accidents, work related accidents, etc.), gunshot wounds, blunt forces to the head in both civilian and military arenas, etc., hematomas can develop around and in the brain tissue. In traumatic brain injury, forces involved in the injury are such that the resulting hematoma or injury can develop pressure inside the cranial cavity which may lead to additional damage of brain tissue. The raised intracranial pressure may cause herniation of the brain out of the foramen magnum because there may not be enough space for the brain to expand. This can result in significant brain damage, coma or death unless an operation is performed to relieve the pressure.

In addition, in traumatic brain injury, shear forces and other vector forces can also lead to conditions of further brain injury. Furthermore, nontraumatic conditions of ischemia (restriction of blood supply) or hypoxia (shortage of adequate oxygen supply) suffered during strokes and other pathologies can also lead to swelling (e.g., edema) within the brain tissue, hence to increased pressure in the cranial cavity. These various pathologies can be rapidly fatal or can lead to permanent neurological injury due to the fact that the brain is housed in a rigid encasement, i.e., the cranium (skull), which has a fixed volume and does not allow for expansion of its contents.

Therefore, not only can a medial practitioner be faced with treating the primary injury or disease but also the medical practitioner may have to deal with secondary effects of swelling, edema, ischemia and hypoxia. Brain swelling or cerebral edema can lead to an increase of intracranial pressure which has been shown to be responsible for instigating the second phase of brain injury leading to permanent damage and death. For example, brain swelling can cause areas near or adjacent to an original injury site to suffer the increasing pressure effects which can lead to a diminished blood supply and lack of nutritional substrate.

The opening of the cranium, i.e., trephination, to relieve intracranial pressure (ICP) is called decompressive craniectomy (DC). In an embodiment of the present invention, the decompressive craniectomy is followed by the reattachment of the inferior portion of the bone flap to the cranium using a movable plate. In one embodiment, the movable plate can be a one way movable hinge, i.e. a unidirectional hinge or a rigid plate attached with partially engaged or loose screws, as will be described in detail in the following paragraphs.

Figure 1:
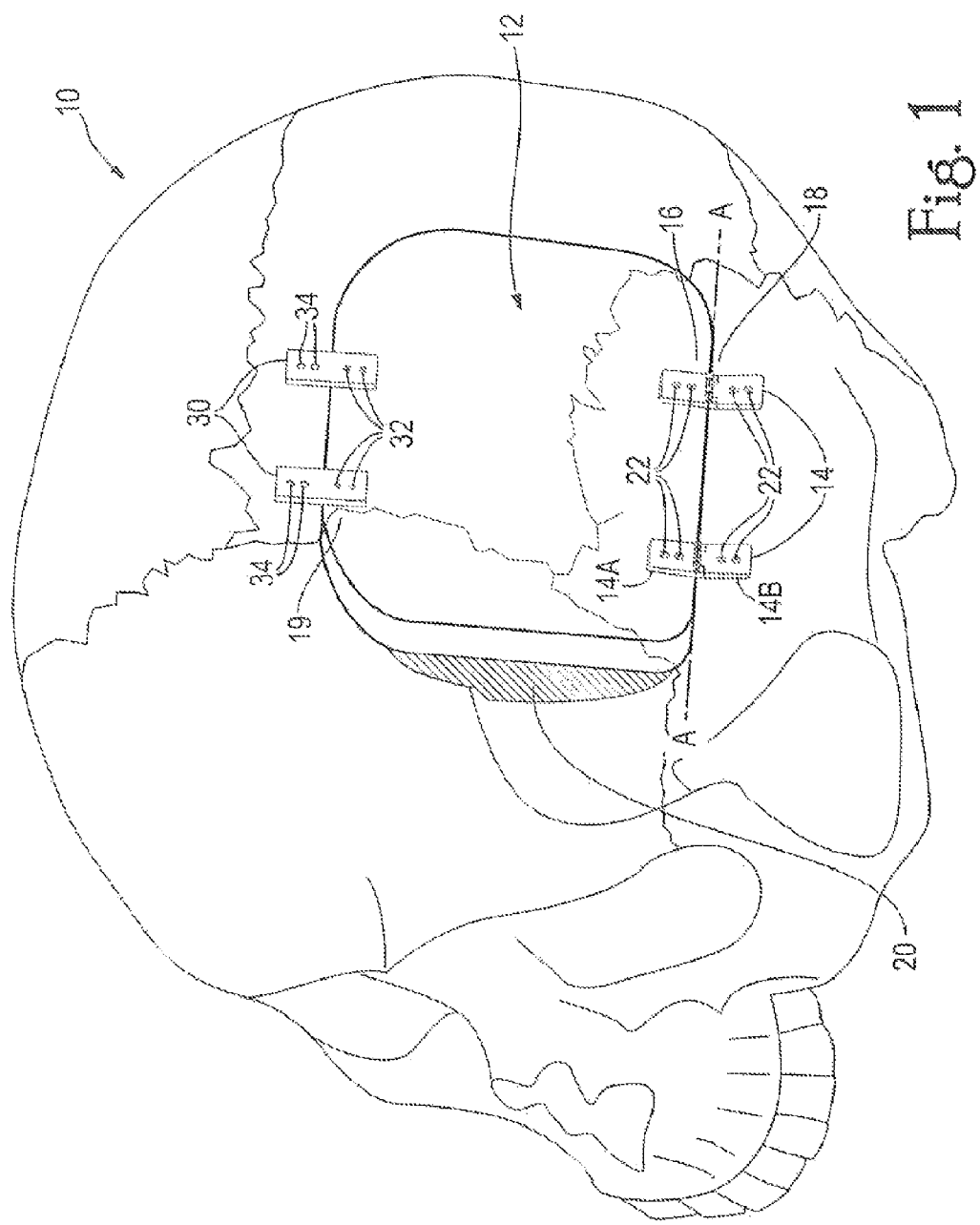
FIG. 1 depicts a bone flap attached to a cranium using a unidirectional hinge, according to an embodiment of the present invention.

FIG. 1 depicts a bone flap 12 attached to cranium 10 using unidirectional hinge 14, according to an embodiment of the present invention. In this embodiment, the lower portion 16 of the bone flap 12 is attached to portion 18, located at a periphery of opening 20, i.e. craniectomy in cranium 10, using the hinge 14. The hinge 14 can be made from various materials including, but not limited to, metals such as titanium, titanium alloys, stainless steel, plastics, ceramics, organic bioabsorbable substrates or any combination thereof. The hinge 14 is attached to portion 18 of cranium 10 and portion 16 of bone flap 12 using fasteners 22. Fasteners 22 are any suitable fasteners for attaching a bone plate to the cranium (skull) 10. Suitable fasteners include, but are not limited to, bone screws, pins, rivets, sutures, wires and the like. The fasteners can be made of titanium, titanium alloy, stainless steel, plastics, ceramics, organic bioabsorbable substrates and the like. The fasteners 22 can be made from a same material as the hinge 14 or from a different material. The fasteners 22 attach one plate 14A of the hinge 14 to the portion 16 of the bone plate 12 and attach another plate 14B of the hinge 14 to the peripheral portion 18 of cranium 10 via beveled holes 23 (shown in FIG. 2) provided in the hinge plates 14A and 14B which allow fasteners 22 to be recessed planar to the plate upon final tightening.

In FIG. 1, two hinges 14 are illustrated being used to attach the bone flap 12 to the cranium 10. However, it must be appreciated that any number of hinges 14, i.e. one or more hinges, can be used. For example, if the bone flap 12 is relatively small, one hinge 14 may be sufficient to hold the bone flap 12 so as to allow the bone flap 12 to rotate around an axis of rotation of the hinge 14 without, for example, lateral tilting. On the other hand, if the bone flap 12 is relatively large, such as the one depicted in FIG. 1, two or more hinges 14 may be used to hold the bone flap 12 to provide a more stable rotation of the bone flap 12 around axis of rotation AA defined by the hinges 14.

Figure 2:
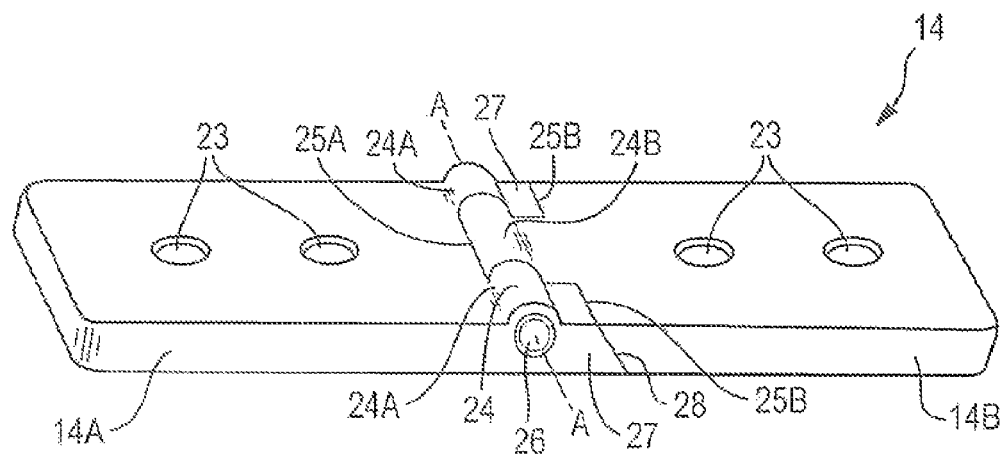
FIG. 2 shows a perspective view of a hinge, according to an embodiment of the present invention.
Figure 3:
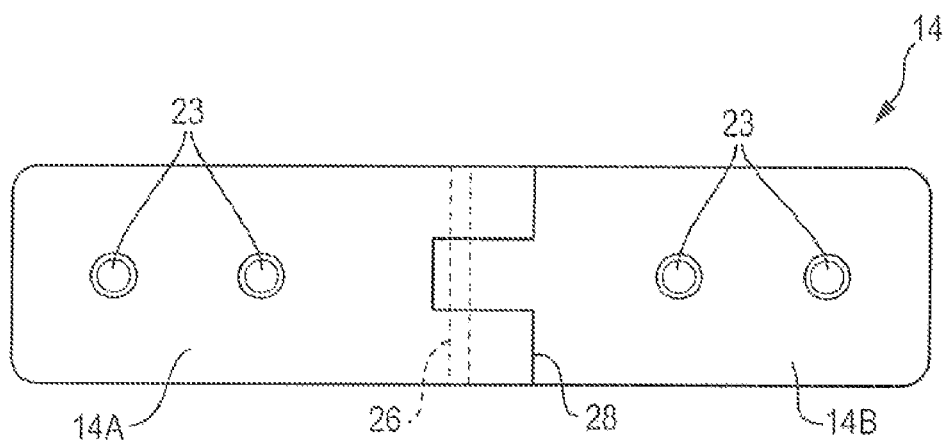
FIG. 3 shows an underside view of the hinge depicted in FIG. 2.

In one embodiment of the invention, hinge 14 is a unidirectional hinge. Specifically, the hinge 14 is configured to rotate at an angle of less than or equal to approximately 180°. FIG. 2 shows a perspective view of the hinge 14, according to an embodiment of the present invention. FIG. 3 shows an underside view of the hinge 14. As stated above, the hinge 14 has hinge plates 14A and 14B. Hinge plates 14A and 14B are terminated by knuckle portions 24A and 24B, which are complementary to each other, when joined together form a barrel portion 24. The barrel portion 24 is configured to receive a pin 26. The pin 26 defines the axis AA of rotation of the hinge 14. Specifically, the pin 26 defines the axis of rotation AA of hinge plate 14A relative to hinge plate 14B.

Hinge plate 14A has an end portion 25A with a semi-cylindrical shape that complements the cylindrical shape of knuckle portion 24B thus allowing the knuckle portion 24B of hinge plate 14B to rotate freely around pin 26. On the other hand, hinge plate 14B has end portions 25B which are substantially flat. In addition, the knuckle portions 24A are provided with projections 27. When the hinge plates 14A and 14B are joined together through the pin 26 and are held in a 180° conformation, i.e., when the hinge plates 14A and 14B are laid flat relative to each other, projections 27 of knuckle portions 24A of hinge plate 14A abut against end portions 25B of hinge plate 14B. Hence, a rotation of the hinge plates 14A and 14B relative to each other is limited to angles between about 0° and about 180° in an outward direction. In other words, the hinge plates 14A and 14B can move from a folding position in which the hinge plates 14A and 14B are superposed (forming an angle of about 0° between each plate) to an extending position in which the two hinged plates 14A and 14B are extended relative to each other (forming an angle of about 180° between each plate). In this embodiment, an interface 28 where the projections 27 of knuckle portions 24A and end portions 25B of hinge plate 14B meet is shown to be substantially flat. However, it must be appreciated that any conformation of the interface 28 is also within the scope of the present invention. For example, the interface 28 may be in another configuration such as, for example, curved or angled configuration. In addition, the interface 28 may have a saw-teeth configuration in which, for example, the teeth can be arranged parallel to each other and extending along the axis of rotation AA of the hinge 14. Furthermore, it must be appreciated that the knuckle portions 24A does not require the projections 27 to function in the manner described. Indeed, instead of projections 27, the knuckle portions 24A may be provided with a straight edge only such that the portion 25B abuts against the straight edge of the knuckle portion 24A thus limiting the relative rotation of the hinge plates 14A and 14B to an angle of less than or equal to approximately 180°. Furthermore, the hinge 14 can be made in an interwoven braided wire configuration. For example, the hinge plates 14A, 14B can be made in an interwoven braided wire configuration. The braided wires can be made from any material including, but not limited to, titanium, titanium alloys, stainless steel, plastics, ceramics, organic bioabsorbable substrates or any combination thereof.

Although hinge plates 14A and 14B are shown in FIGS. 1-3 having generally a rectangular shape, it must be appreciated that the hinge plate 14A and/or the hinge plate 14B can be formed in other shapes such as, a semicircular shape, a semi-rounded shape, a polygonal shape, or the like. Furthermore, a thickness of hinge plates 14A and 14B can be selected as desired according to the application sought. For example, the thickness of the hinge plates 14A and 14B can be selected according to the weigh and/or size of the bone flap 12, etc.

A procedure for attaching the hinge apparatus 14 to the bone flap 12 and to the cranium 10 is described in the following paragraphs.

Patients with intracranial hematoma or infarct pathology related to traumatic brain injury or stroke are brought to an operation room (OR) and undergo emergency cranial surgery, i.e. craniotomy.

After opening the cranium and removing an appropriate bone flap, the dura mater is opened (for example, in stellate fashion) and various hematomas in the brain tissue are addressed to relieve intracranial pressure (ICP). The various hematomas may include epidural hematoma (EDH), subdural hematoma (SDH) and/or intra-cerebral hematoma (ICH). EDH is a buildup of blood occurring between the dura mater and the skull which can lead to an increase in pressure in the intracranial space and ultimately to compression of delicate brain tissue. EDH are usually caused by tears in arteries. SDH is a form of traumatic brain injury in which blood collects between the dura mater and the arachnoid (the middle layer of the meninges). Unlike in EDH, which is usually caused by tears in arteries, SDH usually results from tears in veins that cross the subdural space. This bleeding can lead to a separation of the dura mater and the arachnoid layers. Subdural hemorrhages may cause an increase in intracranial pressure, which can also lead to compression of and damage to delicate brain tissue. ICH is a bleeding within the brain. Once the EDH, SDH and/or ICH are addressed, a duraplasty is done using a collagen-based dural graft matrix. Of course any appropriate covering can be used. For example, galea graft from the patient may be harvested as a dural graft and sutured to edges of the opening in the dura mater.

The bone flap 12 which is removed during the opening of the cranium 10 is re-attached to the inferior cranial edge 18, using hinges 14, as shown in FIG. 1. In one embodiment, self drilling screws 22 are used to attach one hinge 14 to the cranial edge 18 and to the bone flap 12, at one extremity of the of the bone flap 12. In one instance, 5 mm screws are used. However, it must be appreciated that screws with other dimensions or configurations can be used. Specifically, the 5 mm screws are used to attach the hinge plate 14B of the hinge 14 to the inferior cranial edge 18 located at a periphery of opening 20 and to attach the hinge plate 14A of the hinge 14 to the lower portion 16 of the bone flap 12. In one embodiment, the screws used for attaching the hinge plate 14B to the inferior cranial edge 18 can be left untightened, for example extending 1 to 2 mm above the hinge plate 14B, so as to allow some free movement of the bone flap 12 in the vicinity of the inferior edge 18. This operation is repeated and another hinge 14 can be used to secure another extremity of the bone flap 12 to the cranial edge 18. Although, two hinges 14 are illustrated herein being used to secure the bone flap 12 to the skull 10, it must be appreciated that one or more hinges may be used as deemed necessary by the health practitioner. Optionally, one or more plates 30 of any configuration or interlocking wire clasps can also be fastened to superior edge 19 of the bone flap 12 using, for example, screws 32. The one or more plates 30 can be made from any suitable material including, but not limited to, titanium, titanium alloys, stainless steel, plastics, ceramics, or organic bioabsorbable substrates, or any combination of two or more thereof. The one or more plates 30 are left unfastened to the cranium 10 so as to allow the superior edge 19 of the bone flap 12 to move freely. Although the plates 30 are shown in FIG. 1 being fastened "vertically" such that one end of the plates 30 abuts against the skull 10, it must be appreciated that the plates 30 can be fastened "horizontally" or in a reverse direction so that the plates do not abut against the skull 10, positioned with the unfastened end facing inferiorly over bone flap 12. In which case, the plates 30 are oriented so as to not "push" exert pressure or force against or indent the skin scalp of the head when the swollen brain pushes against the flap 12.

As stated above, because hinge 14 is a unidirectional hinge and rotates only at angles less than or equal to approximately 180°, the hinge plate 14A and the hinge plate 14B are attached in such a way that the superior edge 19 of the bone flap 12 is allowed to move outwardly away from the cranium 10 but is restricted from moving inwardly towards the cavity of the cranium past the external surface of the cranium 10. Specifically, the hinge plates 14A and 14B are attached to the inferior edge 18 of the cranium 10 and to the lower edge 16 of the bone flap 12 such that the underside of the hinge plates 14A and 14B comes in contact with the bone flap 12 and in contact with the cranium 10.

In this way, the superior edge 19 of the bone flap 12 is allowed to float or move outwardly to accommodate brain swelling or other intracranial pathology while limiting excursion of the bone flap inwardly towards the brain thus not exercising additional pressure against the brain. Furthermore, the presence of plates 30 further limits the possible inward excursion of the bone flap 12 when the swelling of the brain subsides, thus further eliminating any pressure that may be exercised on the brain by the weight of the bone flap 12. In addition, the bone flap 12 is kept in the surgical field, hinged to the cranium 10 under the protection of the scalp. By keeping the bone flap in the surgical field, future reconstitution of the cranial vault can be done by performing a minor surgical procedure under local anesthesia. Maintaining the bone flap in situ throughout patient's hospital course lessens the risk of injury to an otherwise unprotected brain, minimizes the chances of significant deformity while still providing enlargement the skull volume and thus decompression of the injured brain. Following securing of the bone flap 12 using the one or more hinges 14 and optionally attaching of the plate 30, the opening in the skin of the head is closed by suturing the skin on top of the bone flap 12.

After the patients enter the rehabilitative treatment, the re-attachment of the superior edge 19 of the bone flap 12 is established on an individual basis, using minimally invasive techniques and tools, as described in the following paragraphs. Each patient is brought back to the OR and depending on the patient status, general or local anesthesia is administered for the re-attachment procedure. After sterile preparation and appropriate drape, a lateral fluoroscopic image of the skull is taken to localize the plates 30 unfastened to the skull 10, at the superior edge 19 of the bone flap 12. Upon identification of the plates 30, a one-centimeter opening, for example, is made in the previous incision using a scalpel. The plate or plates 30 are then secured to the skull 10 using, for example, self-drilling screws. If the plates 30 were previously affixed in the "horizontal" or reverse conformation, the plates 30 are rotated by approximately 90° or by approximately 180° in a "vertical" conformation so that a portion of the plate 30 abuts against the cranium 10. Once this rotation is completed, the plates 30 are then attached to the cranium 10. The self-drilling screws are inserted through holes 34 in the plate 30 and screwed to the cranium 10. Hence, the bone flap 12 is affixed to cranium 10 and is "locked" in place and does not move. The wound is then closed in standard fashion. Conventional wound care follows and the patient that underwent the re-attachment procedure may be eligible for discharge the day of surgery.

In an alternative embodiment, instead of attaching the bone flap 12 to the cranium 10 by using the hinge or hinges 14, the bone flap 12 can be attached to the cranium 10 via one or more rigid plates 40, as shown in FIG. 4. Self drilling screws 42 can be used to attach the rigid plate to the inferior cranial edge 18 and to inferior edge 16 of the bone flap 12. In this case, the screws 44 used for attaching the rigid plate 40 to the inferior cranial edge 18 are left untightened, i.e., loose, for example extending 1 to 2 mm above their seat in rigid plates 40. In this way, the bone flap 12 can have some free movement so as to accommodate the swelling of the brain or other intracranial pathology while limiting to a certain extent inward incursion of the bone flap 12 when the swelling of the brain subsides. Specifically, the bone flap 12 can move outwardly away from the cranium 10 because the bone flap 12 and the rigid plate 40 held to the cranium via the loose screws 44 can move with respect to cranium 10 but the bone flap 12 is restricted from moving inwardly towards the cavity of the cranium 10 past a certain extent defined by the protrusion of the screws 44 used for attaching the rigid plate 40 to the inferior cranial edge 18. Just as the cranioplasty or refastening is done with minimally invasive technique, the above described decompressive craniectomy procedure can be accomplished using minimally invasive procedures and techniques with drills, retractors and/or other instruments modified to operate through small portal access or with endoscopic devices.

This operation can be repeated as need and another rigid plate 40 can be used to secure another extremity of the bone flap 12 to the cranial edge 18. Similar to the embodiment depicted in FIG. 1, one or more plates 30 can optionally be fastened to superior edge 19 of the bone flap 12 using, for example, screws 32. The one or more plates 30 are left unfastened to the cranium 10 so as to allow the superior edge 19 of the bone flap 12 to move outwardly freely. Following securing of the bone flap 12 using one or more rigid plates and optionally attaching the plate 30, the opening in the skin of the head is closed by suturing the skin on top of the bone flap 12.

Once the swelling subsides, the patient is brought back to the OR and an incision is made in the skin of the head and the loose screws 44 that are used to attach the rigid plate 40 to the cranium 10 are tightened. In this way, the bone flap 12 is secured to the cranium 10 and is not allowed to move.

If plates 30 are additionally used, another incision is performed to attach the plates 30 to the cranium 10. Specifically, the plates 30 that were previously affixed in the "horizontal" or reverse conformation, as depicted in FIG. 4, are rotated by approximately 90° or by approximately 180° in a "vertical" conformation so that a portion of the plate 30 abuts against the cranium 10, as shown by the arrows in FIG. 4. Once this rotation is completed, the plates 30 are then attached to the cranium 10, for example by using self drilling bone screws. Hence, the bone flap 12 is affixed to cranium 10 and is "locked" in place and does not move. However, plates 30 can be omitted. If bioabsorbable plates, hinges, clasps or fasteners are used at bone edge 16, the absorptive properties of such material may eliminate movement by decomposing, solidifying, hardening or the like. Thus, fastening of bone edge 19 would be unnecessary. Indeed, due to individual patient healing characteristics, fastening of bone edge 19 may not be required using any of the devices at bone edge 16 and can be left to the neurosurgeon's judgment.

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. Thus, the present invention should not be limited by any of the above-described exemplary embodiments.

In addition, although words such as superior, inferior, lower and upper are used to describe embodiments of the invention with reference to the drawings where the bone flap opens in a vertical direction, it must be appreciated that the description is not bound by the use of these words. To the contrary, the description encompasses any situation. For example, instead of lower, upper, inferior and superior words such as left, right, extreme left, extreme right, etc. may be used instead to describe embodiments in which the bone flap opens laterally or located in the parietal, occipital, frontal, temporal or any other anatomical cranial landmark.

Moreover, the methods and systems of the present invention, like related systems and methods used neurosurgery are complex in nature, are often best practiced by empirically determining the appropriate values of the operating parameters to arrive at best design for a given situation. Accordingly, all suitable modifications, combinations and equivalents should be considered as falling within the spirit and scope of the invention.

In addition, it should be understood that the figures, are presented for example purposes only. The architecture of the present invention is sufficiently flexible and configurable, such that it may be utilized in ways other than that shown in the accompanying figures.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope of the present invention in any way.

What is claimed is:

1. A method of performing a decompressive craniectomy, comprising:
    removing a bone flap from a cranium;
    fixing one end of a movable plate directly to one end of the bone flap; and
    attaching another end of the movable plate to the cranium, wherein the movable plate is configured to allow another end of the bone flap not attached to the movable plate to freely move away from the cranium so as to float with intracranial contents.

2. The method of claim 1, wherein the removing of the bone flap from the cranium comprises opening the cranium using an opening device and exposing the intracranial contents in order to gain access to the brain pathology.

3. The method of claim 2, wherein the opening of the cranium using an opening device comprises opening the cranium using an opening device adapted to operate through a portal access or adapted to operate with an endoscopic device.

4. The method of claim 1, wherein the fixing of the one end of the movable plate comprises fixing a first hinge plate of a unidirectional hinge to one end of the bone flap.

5. The method of claim 4, wherein the fixing of the first hinge plate to the bone flap comprises fixing the first hinge plate using bone fasteners.

6. The method of claim 5, wherein the bone fasteners comprise self drilling screws.

7. The method of claim 5, wherein the bone fasteners are made from a material selected from the group comprising titanium, titanium alloy, stainless steel, organic bioabsorbable substrates, or suture, or any combination of two or more thereof.

8. The method of claim 4, wherein the attaching of the other end of the movable plate comprises attaching a second hinge plate of the unidirectional hinge to the cranium.

9. The method of claim 8, wherein the attaching of the second hinge plate to the cranium comprises attaching the second hinge plate using bone fasteners.

10. The method of claim 9, wherein the bone fasteners comprise self drilling screws.

11. The method of claim 9, wherein the bone fasteners are made from a material selected from the group comprising titanium, titanium alloy, stainless steel, organic bioabsorbable substrate, or suture, or any combination of two or more thereof.

12. The method of claim 1, wherein the movable plate is a unidirectional hinge, the unidirectional hinge being rotatable between approximately 0° and approximately 180° such that the bone flap is allowed to move outwardly away from the cranium and is restricted from moving inwardly towards an interior cavity of the cranium.

13. The method of claim 12, wherein the movable plate is made from a material comprising titanium, titanium alloy, stainless steel, plastics, organic bioabsorbable substrate, or ceramics, or any combination of two or more thereof.

14. The method of claim 1, wherein the movable plate is made in an interwoven braided wire configuration.

15. The method of claim 14, wherein the interwoven braided wire configuration includes wires made from a material comprising titanium, titanium alloys, stainless steel, plastics, ceramics, or organic bioabsorbable substrates, or any combination of two or more thereof.

16. The method of claim 1, wherein the end of the bone flap not attached to the movable plate is able to move inwardly up to a cranium convexity edge when the swelling subsides.

17. The method of claim 12, further comprising attaching a plurality of unidirectional hinges to the cranium and to the bone flap.

18. The method of claim 1, further comprising attaching a plate to another end of the bone flap.

19. The method of claim 18, wherein the plate is made from a material comprising titanium, titanium alloys, stainless steel, plastics, ceramics, or organic bioabsorbable substrates, or any combination of two or more thereof.

20. The method of claim 18, wherein the attaching of the plate comprises attaching one end of the plate to the bone flap using bone fasteners.

21. The method of claim 20, wherein the attaching of the plate comprises attaching the plate such that another end of the plate abuts against the cranium.

22. The method of claim 20, wherein the attaching of the plate comprises attaching the plate such that another end of the plate does not abut against the cranium.

23. The method of claim 18, further comprising suturing a skin of the head on top of the bone flap.

24. The method of claim 23, further comprising opening the skin of the head when the swelling subsides to expose the plate and attaching one end of the plate to the cranium using bone fasteners.

25. The method of claim 22, further comprising rotating the plate such that the other end of the plate abuts against a surface of the cranium and attaching the other end of the plate to the cranium.

26. The method of claim 1, wherein the fixing of the one end of the movable plate comprises fixing one end of a rigid plate to the one end of the bone flap.

27. The method of claim 26, wherein the fixing of the one end of the rigid plate to the bone flap comprises fixing the one end of the rigid plate to the one end of the bone flap using bone fasteners.

28. The method of claim 27, wherein the bone fasteners comprise self drilling screws.

29. The method of claim 27, wherein the attaching of the other end of the movable plate comprises attaching another end of the rigid plate to the cranium.

30. The method of claim 29, wherein the attaching of the other end of the rigid plate to the cranium comprises attaching the other end of the rigid plate to the cranium using bone fasteners.

31. The method of claim 30, wherein the attaching of the other end of the rigid plate comprises attaching loosely the other end of the rigid plate by loosely attaching the bone fasteners to the cranium so as to allow movement the bone flap relative to the cranium.

32. The method of claim 31, wherein the bone fasteners comprise self drilling screws.

33. The method of claim 31, further comprising suturing a skin of the head on top of the bone flap.

34. The method of claim 33, further comprising opening the skin of the head to expose the loosely attached bone fasteners and tightening the loosely attached bone fasteners such that the bone flap is secured to the cranium.

35. The method of claim 34, prior to suturing the skin of the head on top of the bone flap, attaching a plate to another end of the bone flap using bone fasteners.

36. The method of claim 1, further comprising:
  preventing an inner surface of the bone flap from moving radially inwardly beyond an inner surface of the cranium.

37. The method of claim 1, wherein the movable plate is configured to allow the bone flap to rotate about an axis.

* * * * *